United States Patent [19]

Maki et al.

[11] 4,423,252

[45] Dec. 27, 1983

[54] PROCESS FOR PREPARING BISPHENOLS

[75] Inventors: Takao Maki, Fujisawa; Tetsuo Masuyama, Machida; Toshiharu Yokoyama; Yoshiko Fujiyama, both of Yokohama, all of Japan

[73] Assignee: Mitsubishi Chemical Industries Limited, Tokyo, Japan

[21] Appl. No.: 279,692

[22] Filed: Jul. 2, 1981

[30] Foreign Application Priority Data

Aug. 7, 1980 [JP] Japan .................................. 55-108595
Aug. 12, 1980 [JP] Japan .................................. 55-110785

[51] Int. Cl.³ ............................................. C07C 39/16
[52] U.S. Cl. .................................... 568/728; 568/727
[58] Field of Search .................................. 568/727, 728

[56] References Cited

U.S. PATENT DOCUMENTS 3,634,341 1/1972 Gammill et al. .................... 568/728
3,760,006 9/1973 Gammill et al. .................... 568/728
4,045,379 8/1977 Kwantes et al. .................... 568/727
4,239,919 12/1980 Hairston ............................ 568/727

FOREIGN PATENT DOCUMENTS 1183564 3/1970 United Kingdom ................ 568/728

Primary Examiner—Werren B. Lone
Attorney, Agent, or Firm—Oblon, Fisher, Spivak, McClelland & Maier

[57] ABSTRACT

Bisphenols are prepared by condensation of a phenol with a ketone in the presence of a sulfonic acid type cation exchange resin partially modified with a pyridinealkanethiol of the formula:

$$Py-(CH_2)_nSH$$

wherein n is a positive integer and Py is 3-pyridyl when n is 1, or 2-, 3- or 4-pyridyl when n is more than 1.

5 Claims, No Drawings

PROCESS FOR PREPARING BISPHENOLS

BACKGROUND OF THE INVENTION

1. Field of the Invention

This invention relates to a process for preparing bisphenols. More particularly it relates to a process for preparing bisphenols wherein a sulfonic acid type cation exchange resin partially modified with a pyridinealkanethiol is used as a condensation catalyst.

2. Description of the Prior Art

It is well known to use a sulfonic acid type cation exchange resin partially modified with an aminothiol as a catalyst in the condensation of a phenol with a ketone to prepare a bisphenol. For example, Japanese Patent Publication No. 19953/1971 discloses the use of an aminoalkanethiol having 1 to 4 carbon atoms such as 2-aminoethanethiol as an aminothiol modifier useful for the above process and Japanese Patent Laying-Open Publication No. 19189/1977 discloses the use of 4-aminothiophenol for the same reaction. However, as these catalysts still suffer from lower reaction rates and selectivities, a catalyst capable of producing bisphenols at higher reaction rates and with higher selectivities has been sought after.

SUMMARY OF THE INVENTION

Upon our careful analysis, we noted that among these prior art processes the use of a sulfonic acid type cationic exchange resin partially modified with 2-aminoethanethiol as a catalyst may provide an advantageous, commercially feasible process due to its considerable high reaction rate and rather good selectivity attained by the catalyst. As a result of further investigation, however, we have now found that the reaction rate and the selectivity toward bis(4-hydroxyphenyl)alkanes can be still improved by the use as a catalyst of a sulfonic acid type cation exchange resin partially modified with a pyridinealkanethiol of the formula given below and accomplished this invention.

Thus, the present invention provides a process for preparing bisphenols comprising subjecting a phenol and a ketone by the condensation reaction in the presence of a sulfonic acid type cation exchange resin partially modified with a pyridinealkanethiol of the formula:

$$Py-(CH_2)_nSH$$

wherein n is a positive integer and Py is 3-pyridyl when n is 1, or 2-, 3- or 4-pyridyl when n is more than 1.

DETAILED DESCRIPTION OF THE PREFERRED EMBODIMENTS

The present invention will hereinafter be described more fully.

The catalyst used in the process of this invention is a sulfonic acid type cation exchange resin partially modified with a pyridinealkanethiol of the formula: $Py-(CH_2)_nSH$ wherein n is a positive integer and Py is 3-pyridyl when n is 1, or 2-, 3- or 4-pyridyl when n is more than 1 (said pyridinealkanethiol of the above formula being hereinafter referred simply as "pyridinealkanethiol"). Examples of the pyridinealkanethiol include 3-pyridinemethanethiol, 2-(4-pyridyl)-ethanethiol, 2-(3-pyridyl)ethanethiol, 2-(2-pyridyl)-ethanethiol, 3-(4-pyridyl)propanethiol, 3-(3-pyridyl)-propanethiol, 3-(2-pyridyl)propanethiol, 4-(4-pyridyl)butanethiol, 4-(3-pyridyl)butanethiol, 4-(2-pyridyl)butanethiol and the like. Preferred are those of the above formula wherein n is 2 or 3. Of these pyridinealkanethiols, for example, 2-(4-pyridyl)-ethanethiol can be prepared by reacting 4-vinylpyridine with thiourea in the presence of p-toluenesulfonic acid or by reacting γ-picoline with formaldehyde followed by halogenation of the terminal hydroxyl group with thionyl chloride or similar halogenating agent and subsequent reaction with thiourea, while 3-(3-pyridyl)propanethiol can be obtained by reacting 3-(3-pyridyl)propanol with thionyl chloride or the like and then with thiourea. Other pyridinealkanethiols may be prepared in a similar manner.

The sulfonic acid type cation exchange resins include those comprised of styrene-divinylbenzene copolymer as resin matrix such as Diaion®SK104, Diaion®SK106, Diaion®PK228, Diaion®HPK25 and Diaion®HPK55 (manufactured by Mitsubishi Chemical Industries, Limited), Amberlite®200 and Amberlyst®15 (manufactured by Rohm & Haas) and Dowex®70 (manufactured by Dow Chemical); those comprised of perfluoroethylene polymer as resin matrix such as Nafion®501 (manufactured by du Pont) and those comprised of phenol-formaldehyde polymer as resin matrix such as Duolite®C-20 (manufactured by Diamond Shamrock). These sulfonic acid type cationic exchange resins have proton exchange capacities of about 0.5 to 6 meq/g and are suitably used in the process of this invention.

Since most of the sulfonic acid type cationic exchange resins are commercially available in the Na-form, they are transformed into the H-form prior to use by the treatment with an acid such as hydrochloric acid, if necessary. After thorough drying, they can readily be modified by the addition of a pyridinealkanethiol at 50° to 100° C. in an organic solvent such as phenol or methanol in which the pyridinealkanethiol is soluble. On this occasion, the pyridinealkanethiol forms very rapidly and quantitatively an ionic bond with the sulfo group of the cationic exchange resin. Therefore, the amount of a given pyridinealkanethiol that must be added to obtain a desired percent modification (i.e., the percentage of the sulfo groups in the cationic exchange resin which are modified by forming ionic bonds with the pyridinealkanethiol) can readily be determined by calculation using the ion exchange capacity of the sulfonic acid type cation exchange resin. In the process of this invention, 2 to 20% modification is preferred.

The phenol used as a starting material in the process of this invention must not have any substituent at the para-position to the hydroxyl group, but may have one or more substituents such as alkyl or halogen at the ortho- or meta-positions. Examples of such phenol include phenol, o-cresol, m-cresol, o-chlorophenol, m-chlorophenol, o-t-butylphenol, 2,6-xylenol, 2,6-di-t-butylphenol, o-phenylphenol and the like. The ketones which can be used include acetone, ethyl methyl ketone, isobutyl methyl ketone, acetophenone, cyclohexanone, 1,3-dichloroacetone and the like.

The phenol is used in an amount of 3 to 50 moles, preferably 5 to 25 moles per mole of the ketone.

The reaction of the phenol and the ketone according to the process of this invention is carried out at a temperature of 30° to 120° C., preferably 60° to 100° C., usually in an inert gas atmosphere at atmospheric pressure or under a slight positive pressure. The cation exchange resin may be used in the form of a suspended bed or fixed bed. Since the reaction is usually carried out in such condition that the phenol is present in excess, the use of a reaction solvent is not especially required, but any suitable inert solvent may be used, if desired.

When the process of this invention is conducted batchwise, the reaction time is usually in the range of about 0.1 to 20 hours depending on the reaction conditions including the amount of the catalyst used and the reaction temperature. In the cases where the reaction is conducted continuously in a fixed bed reactor, a retention time of about 0.1 to 3 hours is employed.

The reaction mixture may be worked up, after removal of insolubles, if necessary, by distillation to remove unreacted acetone, water, low boiling by-products and the unreacted phenol, leaving a crude bisphenol as the residue. Or phenol-bisphenol adduct may be isolated if applicable. The crude product can be purified by any known procedure such as distillation, crystallization or the like to give a pure bisphenol.

Having generally described the invention, a further understanding can be obtained by reference to certain specific examples which are provided herein for purpose of illustration only and are not intended to be limiting unless otherwise specified.

EXAMPLE 1

A 300 ml four-necked, round-bottom glass flask was charged under nitrogen with 160 g of phenol, 14.3 g of a sulfonic acid type cation exchange resin in H-form having a cation exchange capacity of 5.18 meq/g (Diaion®SK104, Mitsubishi Chemical, transformed into the H-form) and 0.843 g of 3-pyridinemethanethiol and the content of the flask was stirred for 5 hours in an oil bath at 80° C. to modify and swell the resin. Fifteen minutes after the start of the modification, a sample of the solution in the flask was withdrawn and analysis of the sample showed that its total nitrogen content was not more than 2 ppm. Therefore, it was confirmed that the modification of the cation exchange resin with 3-pyridinemethanethiol had already been completed at that time.

Subsequently, the temperature of the oil bath was decreased to 60° C. and 3.91 g of acetone was added to the flask to initiate the reaction between phenol and acetone. At each time of 30, 60 and 120 minutes after the start of the reaction, a 2 ml sample of the reaction solution was withdrawn and dissolved in 5 ml of 2-ethylhexanol to give a sample solution for analysis. The unreacted acetone therein was determined by vapour phase gas chromatography and 2,2-bis(4'-hydroxyphenyl)propane (i.e., bisphenol A, hereinafter referred to as pp' isomer) and 2-(2'-hydroxyphenyl)-2-(4'-hydroxyphenyl)propane (hereinafter referred to as op' isomer) were determined by liquid chromatography. The results are shown in Table 1 below. The lengths of time required to reach 80%, 90% and 95% conversion of acetone ($\theta_{80}$, $\theta_{90}$ and $\theta_{95}$) were determined on the time-conversion curve of acetone. These figures are also included in Table 1. No 3-pyridinemethanethiol was detected in the reaction solution, which showed that 3-pyridinemethanethiol had not been eluted from the cation exchange resin during the reaction.

EXAMPLE 2

The procedure of Example 1 was repeated except that the modification of the resin was carried out by the following procedure. The swelling of the cation exchange resin was conducted at first in phenol at 80° C., then decreasing the temperature to 60° C., adding 0.843 g of 3-pyridinemethanethiol, stirring the mixture for 10 minutes. Then, the condensation reaction was initiated by the addition of acetone. The results are shown in Table 1.

EXAMPLES 3 AND 4

The procedure of Example 2 was repeated except that the amount of cation exchange resin and 3-pyridinemethanethiol used was varied as indicated in Table 1. The results are shown in Table 1.

EXAMPLE 5

The procedure of Example 2 was repeated except that the cation exchange resin was replaced by 92.6 g of Nafion®501 (manufactured by du Pont, cation exchange capacity 0.80 meq/g). The results are shown in Table 1.

EXAMPLE 6

The procedure of Example 1 was repeated except that the pyridinealkanethiol used as a modifier was replaced by 0.937 g of 2-(4-pyridyl)ethanethiol. The results are shown in Table 1.

EXAMPLE 7

The procedure of Example 2 was repeated except that the modifier was replaced by 0.937 g of 2-(4-pyridyl)-ethanethiol. The results are shown in Table 1.

EXAMPLE 8 TO 11

The procedure of Example 2 was repeated except that the amount of the cation exchange resin used and the type and amount of the modifier used were changed as indicated in Table 1. The results are shown in Table 1.

COMPARATIVE EXAMPLES A AND B

The procedure of Example 2 was repeated except that 4-aminothiophenol or 2-aminoethanethiol was substituted for 3-pyridinemethanethiol. The amounts of the modifier and the cation exchange resin used and the results of the reaction are reported in Table 1.

TABLE 1

| Ex. No. | Modifier (g) | Cation exchange resin (g) | % Modification | Reaction time (min) | % Conversion of acetone | % Selectivity toward bisphenol A pp' isomer | % Selectivity toward bisphenol A op' isomer | pp'/op' ratio | θ 80[1] (min) | θ 90[2] (min) | θ 95[3] (min) | Conditions for modification |
|---|---|---|---|---|---|---|---|---|---|---|---|---|
| 1 | 3-Pyridinemethanethiol 0.843 | Diaion ® SK104 14.3 | 9.1 | 30<br>60<br>120 | 81.8<br>93.1<br>97.8 | 95.6<br>95.6<br>95.1 | 3.3<br>3.6<br>3.8 | 29.0<br>26.6<br>25.0 | 29 | 45 | 73 | 80° C., 5 hr. |
| 2 | 3-Pyridinemethanethiol 0.843 | Diaion ® SK104 14.3 | 9.1 | 30<br>60<br>120 | 79.2<br>93.8<br>99.3 | 95.9<br>95.7<br>95.5 | 3.3<br>3.5<br>3.8 | 29.1<br>27.3<br>25.1 | 31 | 48 | 66 | 60° C., 10 min. |
| 3 | 3-Pyridinemethanethiol 0.422 | Diaion ® SK104 13.65 | 4.8 | 30<br>60<br>120 | 75.4<br>89.5<br>98.6 | 95.5<br>95.3<br>94.9 | 3.8<br>4.0<br>4.5 | 25.1<br>23.8<br>21.1 | 37 | 63 | 88 | 60° C., 10 min. |
| 4 | 3-Pyridinemethanethiol 1.686 | Diaion ® SK104 15.6 | 16.7 | 30<br>60<br>120 | 72.2<br>91.9<br>99.9 | 96.2<br>95.9<br>95.3 | 3.0<br>3.4<br>3.5 | 32.1<br>28.2<br>27.2 | 41 | 54 | 72 | 60° C., 10 min. |
| 5 | 3-Pyridinemethanethiol 0.843 | Nafion ® 501 92.6 | 9.1 | 30<br>60<br>120 | 75.8<br>82.6<br>83.6 | 93.2<br>92.7<br>93.2 | 4.0<br>4.5<br>4.8 | 23.3<br>20.6<br>19.4 | 40 | — | — | 60° C., 10 min. |
| 6 | 2-(4-Pyridyl)ethanethiol 0.937 | Diaion ® SK104 14.3 | 9.1 | 30<br>60<br>120 | 90.6<br>98.3<br>99.9 | 96.8<br>96.8<br>96.5 | 2.3<br>2.4<br>2.7 | 42.1<br>40.3<br>35.7 | 18 | 29 | 40 | 80° C., 5 hr. |
| 7 | 2-(4-Pyridyl)ethanethiol 0.937 | Diaion ® SK104 14.3 | 9.1 | 30<br>60<br>120 | 91.3<br>96.7<br>98.0 | 96.2<br>95.5<br>95.3 | 2.0<br>2.4<br>2.6 | 48.1<br>39.8<br>36.7 | 18 | 29 | 43 | 60° C., 10 min. |
| 8 | 2-(4-Pyridyl)ethanethiol 0.469 | Diaion ® SK104 13.65 | 4.8 | 30<br>60<br>120 | 88.1<br>97.1<br>99.6 | 96.3<br>96.0<br>95.8 | 2.6<br>3.0<br>3.2 | 37.0<br>32.0<br>29.9 | 24 | 31 | 44 | 60° C., 10 min. |
| 9 | 2-(4-Pyridyl)ethanethiol 1.405 | Diaion ® SK104 14.95 | 13.0 | 32<br>60<br>120 | 90.8<br>98.2<br>99.9 | 97.0<br>96.7<br>96.4 | 2.3<br>2.4<br>2.7 | 42.2<br>40.3<br>35.7 | 21 | 29 | 40 | 60° C., 10 min. |
| 10 | 2-(2-Pyridyl)ethanethiol 0.937 | Diaion ® SK104 14.3 | 9.1 | 30<br>60<br>120 | 85.7<br>95.2<br>98.0 | 94.7<br>95.5<br>94.8 | 2.2<br>2.3<br>2.7 | 43.0<br>41.5<br>35.1 | 22 | 39 | 59 | 60° C., 10 min. |
| 11 | 3-(3-Pyridyl)propanethiol 1.032 | Diaion ® SK104 14.3 | 9.1 | 30<br>60<br>120 | 89.0<br>96.7<br>98.3 | 96.7<br>96.6<br>96.2 | 2.0<br>2.1<br>2.5 | 48.4<br>46.0<br>38.5 | 21 | 31 | 47 | 60° C., 10 min. |
| A[4] | 4-Aminothiophenol 0.760 | Diaion ® SK104 14.17 | 8.3 | 30<br>60<br>120 | 58.0<br>78.2<br>91.2 | 92.1<br>92.4<br>92.0 | 6.0<br>6.2<br>6.5 | 15.4<br>14.9<br>14.2 | 63 | 113 | — | 60° C., 10 min. |
| B[4] | 2-Aminoethanethiol 0.520 | Diaion ® SK104 14.3 | 9.1 | 30<br>60<br>120 | 68.5<br>87.5<br>96.6 | 96.5<br>96.1<br>95.7 | 3.0<br>3.4<br>3.8 | 32.2<br>28.3<br>25.2 | 47 | 78 | 90 | 60° C., 10 min. |

[1]Time required to reach 80% conversion of acetone
[2]Time required to reach 90% conversion of acetone
[3]Time required to reach 95% conversion of acetone
[4]Comparative example

Having now fully described this invention, it will be apparent to one of ordinary skill in the art that many changes and modifications can be made thereto without departing from the spirit or scope of the invention as set forth herein.

What is claimed as new and desired to be covered by Letters Patent is:

1. A process for preparing bisphenols, comprising subjecting a phenol and a ketone to condensation in the presence of a sulfonic acid type cation exchange resin partially modified with a pyridinealkanethiol of the formula:

$$Py-(CH_2)_nSH$$

wherein n is a positive integer and Py is 3-pyridyl when n is 1, or 2-, 3- or 4-pyridyl when n is more than 1, at a temperature of 30° to 120° and at atmospheric pressure or a slight positive pressure, said phenol being selected from the group consisting of phenol, o-cresol, m-cresol, o-chlorophenol, m-chlorophenol, o-t-butylphenol, 2,6-xylenol, 2,6-di-t-butylphenol and o-phenylphenol, said ketone being selected from the group consisting of acetone, ethyl methyl ketone, isobutyl methyl ketone, acetophenone, cyclohexanone and 1,3-dichloroacetone.

2. The process of claim 1 wherein the pyridinealkanethiol has the formula:

$$Py-(CH_2)_nSH$$

wherein n is 2 or 3 and Py is 2-, 3- or 4-pyridyl.

3. The process of claim 1 or 2 wherein the phenol is phenol and the ketone is acetone.

4. The process of claims 1 or 2 wherein the percent modification of the sulfonic acid type cation exchange resin with the pyridinealkanethiol is in the range of 2 to 20.

5. The process of claim 1 or 2 wherein the phenol is in an amount of 3 to 50 moles per mole of ketone.

* * * * *